United States Patent [19]

Zilliken

[11] 4,264,509

[45] Apr. 28, 1981

[54] ISOFLAVONES AND RELATED COMPOUNDS, METHODS OF PREPARING AND USING AND ANTIOXIDANT COMPOSITIONS CONTAINING SAME

[75] Inventor: Fritz W. Zilliken, Remagen, Fed. Rep. of Germany

[73] Assignee: Z-L Limited Partnership, Janesville, Wis.

[21] Appl. No.: 29,122

[22] Filed: Apr. 11, 1979

Related U.S. Application Data

[63] Continuation-in-part of Ser. No. 804,594, Jun. 8, 1977, Pat. No. 4,157,984.

[51] Int. Cl.[3] ................... C07D 311/36; C07D 311/58

[52] U.S. Cl. .............................. 260/345.2; 260/345.5; 426/545

[58] Field of Search .......................... 260/345.2, 345.5; 426/545

[56] References Cited

U.S. PATENT DOCUMENTS 3,681,085 8/1972 Gyorgy .................................. 426/46

3,762,933 10/1973 Gyorgy ................................ 426/542

OTHER PUBLICATIONS

Chemical Abstract, 8th Collective Index, vol. 66–75, 1973.

Chemical Abstract, 7th Collective Index, vol. 56–65, 1969.

*Primary Examiner*—Nicky Chan

*Attorney, Agent, or Firm*—Cooper, Dunham, Clark, Griffin & Moran

[57] ABSTRACT

The present invention concerns isoflavones and related compounds useful as antioxidants and in antioxidant compositions including edible fats and oils. Many of these compounds can be recovered from tempeh, a fermented soybean product. Others can be prepared by chemical modification of those recovered from tempeh. Additionally, all of the compounds can be chemically synthesized. The compounds of the present invention may be used to provide enhanced stability for a wide range of substances subject to oxidative deterioration including edible food products, oils and fats.

7 Claims, No Drawings

ISOFLAVONES AND RELATED COMPOUNDS, METHODS OF PREPARING AND USING AND ANTIOXIDANT COMPOSITIONS CONTAINING SAME

BACKGROUND OF THE INVENTION

This is a continuation-in-part of application Ser. No. 804,594, filed June 8, 1977, now U.S. Pat. No. 4,157,984, issued June 12, 1979, the disclosure of which is hereby incorporated by reference into the present disclosure.

Many food products containing and including edible fats and oils, i.e., fats and oils of animal and vegetable origin or modified fats and oils of animal and vegetable origin, become rancid or have an undesirable taste and/or color imparted thereto during storage, especially upon exposure to or on contact with oxygen. A number of chemical compounds have been employed for avoiding or reducing these effects so that food products containing fats or oils may be kept for longer periods of time, but such agents have not been entirely satisfactory or effective in many cases. Furthermore, such chemical compounds are usually synthetic chemical products not derived from or identical with material of natural food classifications and, as a consequence, there has been some question as to the advisability of using such compounds in food compositions.

Principal antioxidants of the above kinds heretofore employed included BHA (butylated hydroxyanisole), BHT (butylated hydroxytoluene) and TBHQ (tertiary butylhydroquinone), as well as some other chemicals of which one example is propyl gallate (PG). While these materials have been quite effective in animal fats, such as lard, they are much less useful in some other applications. Their volatility and tendency to decompose at high temperatures makes them not entirely suitable for deep fat fried foods. Indeed, their usefulness for stability of vegetable oils is less than satisfactory. For example, they are not entirely effective in protecting against off-flavor development, such as the so-called reversion flavor, that occurs, with passage of time, in soybean oil. For these and other reasons, there has been a need for improvement in the field of antioxidants, especially those to be used with food materials that comprise or consist of fats or oils.

It has been heretofore known that antioxidant properties are possessed by tempeh, a fermented soybean product obtained by fermenting soybeans with a fungus, either *Rhizopus oligosporus* or *Rhizopus oryzae.* Food products containing tempeh, such as fish or fatty meat products exhibit improved stability, see U.S. Pat. No. 3,681,085 (1972). Further, it has heretofore been found that by extracting tempeh with a mixture of hexane and methanol, a component of tempeh, namely oil of tempeh, can be recovered, see U.S. Pat. Nos. 3,762,933 (1973) and 3,885,256 (1974), which exhibits enhanced antioxidant properties relative to those of tempeh. This oil of tempeh has been found to be useful in stabilizing a wide variety of edible oils and fats.

SUMMARY OF THE INVENTION

The present invention involves the discovery that numerous isoflavones and related compounds which possess antioxidant properties may be recovered from tempeh. Other compounds which also are useful as antioxidants and/or as components of antioxidant compositions can be prepared by chemical modification of those recovered from tempeh. Additionally, all of the compounds can be chemically synthesized. The compounds of this invention have the structure:

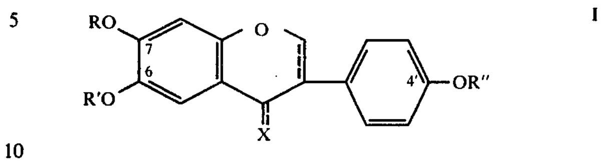

wherein the dashed lines may be carbon-carbon single bonds or carbon-carbon double bonds, and wherein X may be two hydrogen atoms or oxygen, and further wherein each of R, R' and R'' may be a methyl or ethyl group or hydrogen.

These compounds possess antioxidant properties and may be utilized in the stabilization of a wide variety of food products including edible fats and oils.

Of these compounds those having the structure

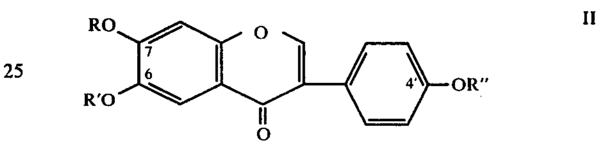

may be recovered from tempeh either individually or as components of a mixture.

Of the compounds so recovered certain are known compounds, such as for example, texasin (6,7-dihydroxy-4'-methoxyisoflavone), genistein (5,7,4'-trihydroxyisoflavone), daidzein (7,4'-dihydroxyisoflavone), glycitein (6 methoxy-7,4'-dihydroxyisoflavone), and the so-called "Murata" compound (6,7,4'-trihydroxyisoflavone). However, the fact that these compounds possess antioxidant properties is a new discovery. Of these compounds, texasin has been found to be a particularly effective antioxidant.

Also, certain compounds having the structure

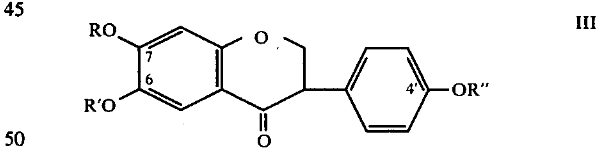

may be recovered from tempeh in minor amounts. However, these compounds are obtained in higher yield upon chemical modification, specifically hydrogenation, of compounds II. Of the compounds III, the compound having the structure

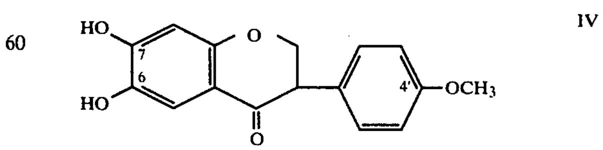

has been found to be particularly effective. All of the compounds III are novel.

Compounds having the structure

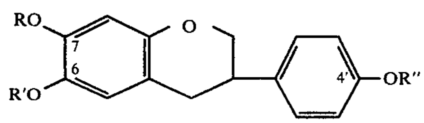

may be prepared by hydrogenation of Compounds IV. Of these, the compound having the structure

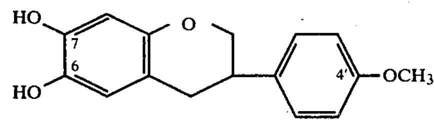

is the most effective of the antioxidants which have been evaluated. All of the Compounds V are also novel.

These Compounds I through VI may be chemically synthesized as well as recovered from tempeh. Thus, in addition to providing compounds useful as antioxidants and in antioxidant compositions, the present invention provides methods of preparing and/or recovering the compounds disclosed.

It is therefore a primary object of the present invention to provide compounds useful as antioxidants.

It is a related object to provide antioxidant compositions which include these compounds.

It is a further related object to provide edible oils, fats and other food products which include these antioxidant compositions.

It is another object of this invention to provide methods of stabilizing edible oils, fats or foods by including in such oils, fats or foods an effective amount of an antioxidant composition.

It is a final object to provide methods of recovering and/or preparing compounds useful as antioxidants.

How these and other objects of this invention are accomplished will become apparent upon reading the detailed description of the invention including the examples set forth, and the claims which follow. In at least one embodiment of the present invention at least one of the foregoing objects will be achieved.

DETAILED DESCRIPTION OF THE INVENTION

In accordance with one embodiment of this invention, isoflavones having the structure

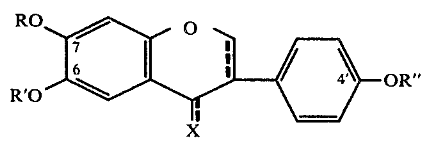

wherein the dashed lines may be carbon-carbon single bonds or carbon-carbon double bonds, and wherein X may be two hydrogen atoms or oxygen, and further wherein R, R' and R" may be a methyl or ethyl group or hydrogen have been found to be useful as antioxidants and as components of antioxidant compositions.

Certain of these compounds, namely those having the structure

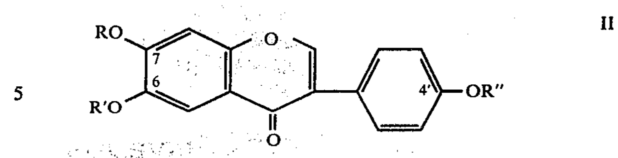

are natural products which may be recovered from tempeh, an Indonesian foodstuff, by fermentation of soybeans with a fungus, e.g. either *Rhizopus oligosporus* ATCC No. 22959 or *Rhizopus oryzae* ATCC No. 9363. Compounds II are typically present as a mixture in tempeh and are most readily recovered therefrom in the form of a mixture from which the individual compounds can subsequently be isolated.

Compounds encompassed within Structure II as well as within the other structures herein may include stereoisomers and optical isomers. For purposes of this disclosure, no distinction will be made among such isomers so that it is to be understood that the disclosure and claims set forth hereinafter embrace all of the isomers encompassed within the structural formulas indicated. Certain of Compounds II are known compounds, such as for example, texasin (6,7-dihydroxy-4'-methoxyisoflavone), genistein (5,7,4'-trihydroxy isoflavone), daidzein (7,4'-dihydroxyisoflavone), glycitein (6 methoxy-7,4'-dihydroxyisoflavone), and the so-called "Murata" compound (6,7,4'-trihydroxyisoflavone). However, in accordance with the present invention it has been discovered that these compounds possess antioxidant properties. Of these compounds, texasin, which has the structure

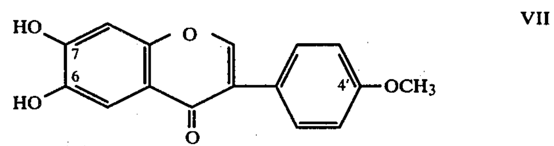

has been found to be a particularly effective antioxidant.

In addition to Compounds II, additional compounds having the structure

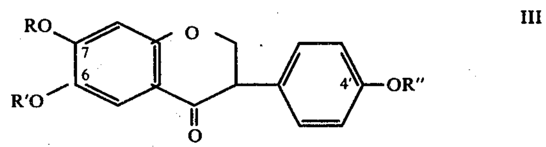

are present in tempeh in minor amounts and may be recovered therefrom. However, these compounds are obtained in higher yield upon chemical modification, specifically, hydrogenation, of Compounds II. Of the Compounds III, the compound produced by hydrogenation of texasin, namely, 6,7-dihydroxy-3-(4-methoxyphenyl)chromanon-4, having the structure

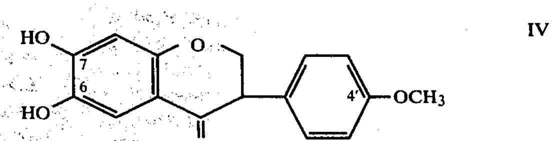

has been found to be particularly effective. Compounds III are novel compounds useful as antioxidants and as components of antioxidant compositions.

Finally, novel compounds having the structure

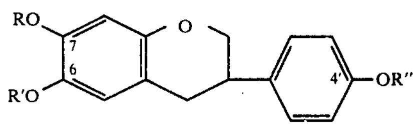

may be prepared by hydrogenation of Compounds III. Of these, the compound, 6,7-dihydroxy-3-(4-methoxyphenyl)chroman having the structure

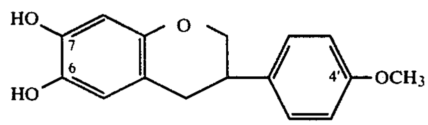

is the most effective of the antioxidants which have been evaluated.

In accordance with another embodiment of this invention, antioxidant compositions may be prepared which include one or more of Compounds I and a suitable carrier. Furthermore, antioxidant compositions which include one or more of Compounds III and/or V provide exceptional antioxidative properties as set forth in the examples hereinafter. Suitable carriers include essentially all non-toxic substances with which the compounds may be admixed or in which they may be dissolved and/or suspended. When the antioxidant composition is intended for use in the stabilization of oils and fats the carrier may be the same or another compatible oil or fat. The amount of the compound or compounds present in the composition may vary within a wide range limited only by the requirement that the amount be effective to provide antioxidant properties to the composition. Typically, amounts will range from about 0.001 to 10 percent by weight.

Stabilized edible fat or oil compositions may be prepared by adding thereto an antioxidant composition which includes one or more of compounds I in an amount effective to stabilize such edible fat or oil. Effective amounts of such antioxidant compositions for improving the stability of oils or fats such as for example, lard, corn oil, olive oil, bean oil, safflower oil, vegetable oil, cottonseed oil, polyunsaturated oils, animal fats or oils and the like are amounts in the range of about 0.01 to 1.0 percent by weight, more or less.

Such antioxidant compositions can also be included in food products to produce stabilized food compositions. Accordingly, food products, such as fish, fatty meat or derivatives thereof, may be stabilized by the addition thereto of an effective amount of an antioxidant composition such as described hereinabove. Effective amounts may typically range from 0.001 to 10 percent by weight, preferably 0.01 to 1.0 percent.

As indicated hereinabove, Compounds II and certain of Compounds III are produced by fermentation of soybeans with a fungus, e.g., *R. oligosporus* or *R. oryzae.* Compounds II may then be recovered in the following manner. Dry, e.g. lyophilized, tempeh powder or cultured fungus is contacted with a 60–70% aqueous methanol solution for an extended period of time, for example, overnight, at a temperature of about 4° C. thereby producing an extract of methanol-soluble components including one or more of the isoflavones II. The methanol extract solution, after removal of insoluble material, is evaporated to dryness, preferably in vacuo, at an elevated temperature, for example, about 40°–60° C. A solid residue is produced most of which is redissolved upon contact with dry methanol. That portion of the residue which is methanol insoluble is separated from the soluble components by centrifugation and discarded. After centrifugation, the methanol supernatant is extracted with haxane several times, for example, two to three times, in order to remove any traces of hexane-soluble impurities, such as lipids. After discarding the resulting hexane extract, the remaining methanol supernatant is evaporated to reduce its volume to a minimal fraction, for example, about 20 ml, and kept at a temperature of about −20° C. for about 15–20 minutes. This results in formation of additional precipitate which is removed and discarded.

The isoflavones may then be recovered from the methanol supernatant or extract as follows. The supernatant is subjected to molecular sieve chromatography, for example, chromatography on Sephadex LH20 using a suitable size column, for example 2×40 cm, and a suitable mobile phase, for example, n-propanol:ethylacetate:water in a ratio 5:5:1. One of the fractions resulting from this chromatographic separation is fluorescent with emission in the blue range of the visible spectrum. This blue fluorescent fraction is separated and subjected to adsorption chromatography on a suitable matrix, for example, silica gel, using an appropriate mobile phase, e.g. ethylacetate:propanol:water=95:2:3. The resulting blue fluorescent fraction is then rechromatographed on an adsorptive matrix, e.g. thin layer chromatography on silica gel, employing a different mobile phase, e.g. cyclohexane:dichloromethane:ethylformate:formic acid=35:30:30:5. Each of the isoflavones can then be recovered in essentially pure form using its differential mobility on the silica gel plate.

Alternatively, Compounds II can be chemically synthesized by forming a suspension of a compound having the structure

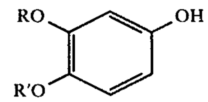

wherein each of R and R' may be either hydrogen or an ethyl or methyl group and a compound having the structure

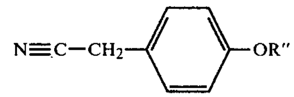

wherein R" may be hydrogen, methyl or ethyl in dry ethylether containing zinc chloride. This suspension is then exposed to dry hydrogen chloride for a sufficient time to form an oily product. The suspension is next maintained at an appropriate temperature for a sufficient time to permit the oil product formed upon exposure to dry hydrogen chloride to separate from the suspension. The supernatant remaining after separation of the oil product from the suspension is removed and discarded. Next, a major amount of water and a minor amount of concentrated hydrochloric acid is added to the oil product to form a mixture, the mixture is boiled under reflux for a sufficient time to produce a precipitate product having the structure

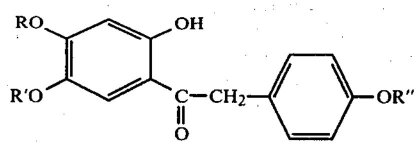

After recovering this precipitate, it is dissolved in a suitable solvent, borontrifluoride-methyletherate added, the temperature adjusted to about 50° C., methanesulphonyl chloride added as a solution, and then the resulting solution heated at about 90°–100° C., for a sufficient time to permit the reaction to proceed substantially to completion. Finally, Compound II is recovered.

Compounds III can be prepared by hydrogenating Compounds II using conventional techniques such as contact with hydrogen gas in the presence of a catalyst under appropriate conditions of temperature, pressure and the like. Similarly, Compounds V can be prepared by hydrogenating Compounds III and/or II.

The following examples are set forth to illustrate the practices of the present invention but are not intended in any way to limit or otherwise restrict the scope thereof as set forth in the preceding description or in the claims which follow.

EXAMPLE I

The compounds 6,7-dihydroxy-3-(4-methoxyphenyl)-chromanon-(4) and 6,7-dihydroxy-3(4-methoxyphenyl)-chroman were evaluated as antoxidants using an automated version of the Swift stability test at 100° C. For a more detailed description of the Swift stability test see A.O.C.S. Tentative Method Cd 12-57 (revised 1959. For the test the lard was heated to 100° C. and air bubbled through at 2 ml/minutes. Every few hours the oil was analyzed for peroxide value using the peroxide value test, A.O.C.S. Official Method Cd8-53 (1960). The tests were carried out using two different batches of lard. The results of the tests are shown in Table I.

TABLE I

AUTOMATED SWIFT STABILITY ON LARD
End of Induction Period in Hours

| BATCH | ANTIOXIDANT | CONCENTRATION OF ANTIOXIDANT 25 mg/kg | 50 mg/kg | 100 mg/kg | 200 mg/kg |
|---|---|---|---|---|---|
| A | 6,7-dihydroxy-3-(4-methoxy-phenyl)chroman | | | 50 | 62 |
| | 6,7-dihydroxy-3-(4-methoxy-phenyl)chromanon-4 | | | 33 | 38 |
| | BHA | | | 26 | 32.5 |
| | BHT | | | 27 | 29 |
| | TBHQ | | 32 | 42 | |
| | α-tocopherol (Vitamin E) | | | 21 | 21 |
| | Blank | | ←2.5→ | | |
| B | 6,7-dihydroxy-3-(4-methoxy-phenyl)chroman | 26 | 43 | 92 | 110 |
| | 6,7-dihydroxy-3-(4-methoxy-phenyl)chroma-non-4 | 15 | 22 | 45 | 62 |
| | BHA | 10 | 30 | 49 | 57 |
| | Blank | | ←6.5→ | | |

According to the results obtained, 6,7-dihydroxy-3-(4-methoxyphenyl)chroman is the most effective of the antioxidants tested. 6,7-dihydroxy-3-(4-methoxyphenyl)chromanon-4 is better than α-tocopherol, but less effective than TBHQ and comparable with BHA and BHT.

EXAMPLE 2

The Swift stability test described for lard in Example 1 was repeated with palm oil and bean oil. The results again indicated that 6,7-dihydroxy-3-(4-methoxyphenyl)chroman is the most effective of the antioxidants. 6,7-dihydroxy-3-(4-methoxylphenyl)chromanon-4 was better than α-tocopherol, but less effective than TBHQ and comparable with BHA and BHT.

EXAMPLE 3

The compounds tested in Example 1, namely, 6,7-dihydroxy-3-(4-methoxyphenyl)chroman and 6,7-dihydroxy-3-(4-methoxyphenyl)chromanon-4, were also tested to evaluate their effect upon the taste of normal quality lard, bean oil and palm oil. The compounds were added to the lard or oil at amounts ranging from 25–200 mg/kg and stored at 15° C. or 50° C. in the dark. The lard or oil was then tasted periodically over a 14-week period. It was found that 6,7-dihydroxy-3-(4-methoxyphenyl)chromanon-4 favorably influenced the taste of the lard and oils. Addition of 6,7-dihydroxy-3-(4-methoxyphenyl)chroman imparted an off-taste although this may be due to the presence of an impurity.

EXAMPLE 4

The same compounds were also evaluated to determine whether they would induce sterility and/or premature abortion of fetuses by feeding the compounds to female rats. In accordance with the Allen-Doisy Test ovarectomized rats were fed the compounds. No negative effect upon the production of female hormones or antifertility activity was noted. Additionally, feeding of the compounds to pregnant rats produced no abortive action.

EXAMPLE 5

The compounds 6,7-dihydroxy-3-(4-methoxyphenyl)-chromanon-(4) and 6,7-dihydroxy-3-(4-methoxyphenyl)-chroman were tested in lard using the Swift Stability Test at a series of concentrations. The results for two series of samples are shown in Tables II and III.

TABLE II

ANTIOXIDANT PROPERTIES OF
6,7-dihydroxy-3-(4-methoxyphenyl)-chroman

| Concentration in Stripped lard [2g] | Protection [percent] | | POV [meq$O_2$/kg] | |
|---|---|---|---|---|
| 0.5 mg = 250 ppm | 96 | | 1.9 | |
| 0.2 mg = 100 ppm | 96 | 98 | 2.2 | 1.0 |
| 0.1 mg = 50 ppm | | 86 | | 6.4 |

TABLE II-continued

| ANTIOXIDANT PROPERTIES OF 6,7-dihydroxy-3-(4-methoxyphenyl)-chroman | | | | |
|---|---|---|---|---|
| Concentration in Stripped lard [2g] | Protection [percent] | | POV [meq$O_2$/kg] | |
| 0.05 mg = 25 ppm | 38 | 33 | 32.8 | 30.5 |
| 0.02 mg = 10 ppm | 22 | | 41 | |
| None | 0 | 0 | 52.6 | 45.4 |

TABLE III

| ANTIOXIDANT PROPERTIES OF 6,7-dihydroxy-3-(4-methoxyphenyl)-chromanon-4 | | | | |
|---|---|---|---|---|
| Concentration in Stripped lard [2g] | Protection [percent] | | POV [meq$O_2$/kg] | |
| 0.5 mg = 250 ppm | 99 | | 0.5 | |
| 0.2 mg = 100 ppm | 94 | 98 | 3.1 | 0.8 |
| 0.1 mg = 50 ppm | | 53 | | 21.3 |
| 0.05 mg = 25 ppm | 44 | 25 | 29.3 | 34.1 |
| 0.02 mg = 10 ppm | 22 | | 41 | |
| None | 0 | 0 | 52.6 | 45.4 |

EXAMPLE 7

An antioxidant composition was obtained from tempeh which included Texasin and additional isoflavones having the structure

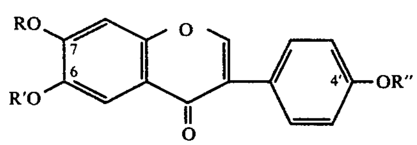

wherein R, R' and R" may be a methyl or ethyl group or hydrogen. This mixture of isoflavones was evaluated using the Swift Stability Test described hereinabove at 110° C. Lard samples containing 500, 50 and 1 ppm of the mixture were prepared by suitable dilutions of a stock mixture of the isoflavone mixture dissolved in 1:1 chloroform-methanol and the mixture was evaporated under vacuum to a clear solution. A similar set of lard samples containing BHT was also prepared for comparison. Results of the test are shown in Table IV.

TABLE IV

| Sample | Concentration Antioxidant (ppm) | Stability (hours) |
|---|---|---|
| Isoflavone mixture | 500 | 36 |
| | 50 | 22 |
| | 1 | 22 |
| BHT | 500 | 81 |
| | 50 | 35 |
| | 1 | 24 |

TABLE IV-continued

| Sample | Concentration Antioxidant (ppm) | Stability (hours) |
|---|---|---|
| Control | 0 | 22 |

It may be seen that the isoflavone mixture at 50 ppm and 1 ppm produced no significant increase in stability. With the 500 ppm sample, however, the stability was comparable to that of the 50 ppm BHT sample. Thus, the isoflavone mixture has antioxidant properties, but its activity is less than that of BHT under conditions of the test. It should be noted that this test is not completely suitable for evaluating isoflavones under all conditions because of the severity of the conditions used (temperature 110° C. with air bubbled through the sample).

EXAMPLE 8

An antioxidant composition was obtained from tempeh which included Texasin and trihydroxy-isoflavone. This mixture of isoflavones was evaluated using the Oven Storage Test described hereinabove at a temperature of 60° C. for 3 days. Peroxide values were determined for stripped lard samples containing the mixture. The results are set forth in Table V.

TABLE V

| Stripped Lard [g] | Concentration Antioxidant [mg] | =ppm | Protection [percent] |
|---|---|---|---|
| 1.0 | 0.5 | 250 | 98 |
| 1.5 | 0.25 | 125 | 96 |
| 1.8 | 0.10 | 50 | 49 |

EXAMPLE 9

A series of isoflavones either recovered from tempeh or chemically synthesized were evaluated using the Oven Storage Test for 40 hours and for 3 days at 60° C. In order to dissolve the isoflavones in 2 kg of stripped lard an emulsifier was employed such as a glycerol. The results are shown in Table VI.

TABLE VI

| ANTIOXIDANT PROPERTIES OF ISOFLAVONES | | | | | | | | | | | | | | | |
|---|---|---|---|---|---|---|---|---|---|---|---|---|---|---|---|
| Amount Isoflavone | Conc. | % Protection (40h, 60° C.) SAMPLE | | | | | | | % Protection (3days, 60° C.) SAMPLE | | | | | | |
| [mg] | [% lard] | 1 | 2 | 3 | 4 | 5 | 6 | 7 | 1 | 2 | 3 | 4 | 5 | 6 | 7 |
| 1.0 | 0.05 | 21 | 21 | 0 | 100 | 91 | 45 | 67 | 28 | 21 | 31 | 99 | 77 | 50 | 20 |
| 0.5 | 0.025 | — | — | — | 95 | 90 | — | 57 | — | — | — | 91 | 75 | — | 9 |
| 0.1 | 0.005 | 0 | 0 | 8 | 43 | 0 | 15 | 17 | 0 | 22 | 46 | 29 | 1 | 2 | 0 |
| 0.05 | 0.00025 | — | — | — | — | — | — | 17 | — | — | — | — | — | — | 0 |

1 6-methoxy-7,4'-dihydnoxyisoflavone (glycitein)
2 7-methoxy-6,4'-dihydroxyisoflavone (kakkatin)
3 6,7-dimethoxy-4'-hydroxyisoflavone
4 isoflavone mixture chemically synthesized without #7
5 6,4'-dimethoxy-7-hydroxyisoflavone
6 isoflavone mixture from tempeh
7 6,7,4'-trihydroxyisoflavone The test results indicate that each of the isoflavones has antioxidant properties. Particularly effective is the isoflavone mixture obtained by chemical synthesis which includes various methoxy-substituted isoflavones. Also, the compound 6,4'-dimethoxy-7-hydroxyisoflavone was particularly effective.

EXAMPLE 10

Synthesis of 1,2,4-trihydroxybenzene

Fifty grams (0.46 mol) of 1,4-benzoquinone was slowly added with continuous stirring and cooling to a mixture consisting of 150 g acetic acid anhydride and 3 ml concentrated sulfuric acid. During this reaction the temperature should be maintained between 40° and 50° C. After all of the quinone has been dissolved and the heat development has ceased, the reaction mixture was poured into two liters of water and the precipitate formed was filtered off. After drying in a vacuum desicator one obtained 1,2,4-triacetoxybenzene in the form of a light brown amorphorus power which may be recrystallized from methanol.

Eighty grams of the crude 1,2,4-triacetoxybenzene were dissolved in 200 ml of methanol containing 6 g of concentrated sulfuric acid. The reaction mixture was boiled under reflux for one hour. Then the solution was cooled to room temperature and neutralized with an equivalent amount of fine powdered sodium carbonate. Thereafter 800 ml of ethylether was added whereupon sodium sulfate precipitated out, which was removed by filtration. Reaction by-products and contaminants being responsible for a dark red coloration may be removed employing solid silica gel. After evaporation of the supernatant under reduced pressure, a dark red oil is obtained which crystallized upon standing at 40° C. in the form of a slight reddish solid mass which is pure enough for the next step. This product is 1,2,4-trihydroxybenzene.

EXAMPLE 11

Synthesis of 6,7-dihydroxy-4'-methoxyisoflavone (6,7-dihydroxy-3-(4-methoxyphenyl)chromone)

35.4 grams of 1,2,4-trihydroxybenzene were suspended in 200 ml of dry ethylether containing 30 g of dry zinc-chloride (0.22 mol) and 50 g (0.34 mol) of p-methoxyphenylacetonitrile. The suspension was then exposed for 4 hours at 0° C. to a gentle stream of dry hydrogen chloride (HCl), the gas bubbling through the suspension under continuous stirring. Then the reaction mixture was kept for 70 hours at 4° C. and thereafter the supernatant was decanted from the heavy oil which had separated. The oil was washed twice with ethylether, then one liter of water and a few ml of concentrated hydrochloric acid were added and the mixture boiled for 1 hour under reflux. After cooling to room temperature the precipitate was collected by filtration and recrystallized from ethanol/water. This precipitate was (4-methoxybenzyl)-2,4,5-trihydroxyphenyl ketone.

Four grams (14.6 milimol) of (4-methoxybenzyl)-2,4,5-trihydroxyphenyl ketone were dissolved in 50 ml. of dry dimethylformamide. To this solution was added 7.5 grams of borontrifluoride-methyetherate $BF_3$-$(CH_3)_2O$ dropwise. Under spontaneous elevation of the temperature the color of the solution turns to yellowish-green. Then the temperature of the reaction is adjusted to 50° C. and a solution of 5 grams methanesulphonyl chloride ($CH_3SO_2Cl$) in 25 ml of dry dimethylformamide (DMF) is added dropwise. Thereafter, the solution is heated for 90 minutes at 90°-100° C. After cooling to room temperature, the reaction mixture is poured into 500 ml water and the resulting yellow precipitate is filtered off. After drying in a desicator the crude product is purified by boiling in 50 ml methanol and then 50 ml of ethyl ether. The resulting white powder can be recrystallized from dioxane or glacial acetic acid. This product is 6,7-dihydroxy-3-(4-methoxyphenyl)chromone (texasin).

EXAMPLE 12

Synthesis of 6,7-dihydroxy-3-(4-methoxyphenyl)chromanon-4

Six grams of texasin (6,7-dihydroxy-3-(4-methoxyphenyl)chromone) were dissolved and partially suspended in 500 ml of ethanol and hydrogenated at normal pressure and room temperature using 10% palladium/charcoal as a catalyst under addition of 6 drops of triethylamine. The catalytic hydrogenation is continued until no starting material is detectable by means of thin layer chromatography. Thereafter, the catalyst is removed by filtration, an equal amount of water is added to the reaction mixture and the solution is evaporated under reduced pressure. After removal of the largest part of the ethanol the product precipitates out in pure form. After filtration and drying in a desicator 5.5 grams of a light yellow powder is obtained which may be recrystallized once from ethanol/water. The product has the formula $C_{16}H_{14}O_5$, molecular weight 286, and melting point 215° C. It was characterized by UV, NMR, IR and Mass spectroscopy and determined to be 6,7-dihydroxy-3-(4-methoxyphenyl)-chromanon-4. The product is actually a mixture of optical isomers but since the isomers exhibit the same properties further characterization was not deemed necessary for purposes of this disclosure. Therefore it is to be understood that the scope of the disclosure and claims embraces the optical isomers of the compounds discussed herein.

EXAMPLE 13

Synthesis of 6,7-dihydroxy-3-(4-methoxyphenyl)chroman

Fifteen grams of texasin (6,7-dihydroxy-3-(methoxyphenyl)chromone) were dissolved and partially suspended in 500 ml of ethanol and hydrogenated at normal pressure and room temperature using 10% palladium/charcoal as a catalyst under addition of 20 drops of concentrated sulfuric acid. The catalytic hydrogenation is continued until neither texasin nor any of the 6,7-dihydroxy-3-(4-methoxyphenyl)chromanon-4 was detected by thin layer chromatography. The further purification was identical to that described in Example 12. The product has the formula $C_{16}H_{16}O_4$, molecular weight 272, and melting point 160° C. It was characterized by UV, NMR, IR and Mass spectroscopy and determined to be 6,7-dihydroxy-3-(4-methoxyphenyl)-chroman. As in Example 12, the product is actually a mixture of optical isomers but since the isomers exhibit the same properties further characterization was not deemed necessary for the purposes of this disclosure. Therefore, it is to be understood that the scope of the disclosure and claims embraces the optical isomers of the compounds discussed herein.

EXAMPLE 14

Synthesis of 6,7-dihydroxy-isoflavone

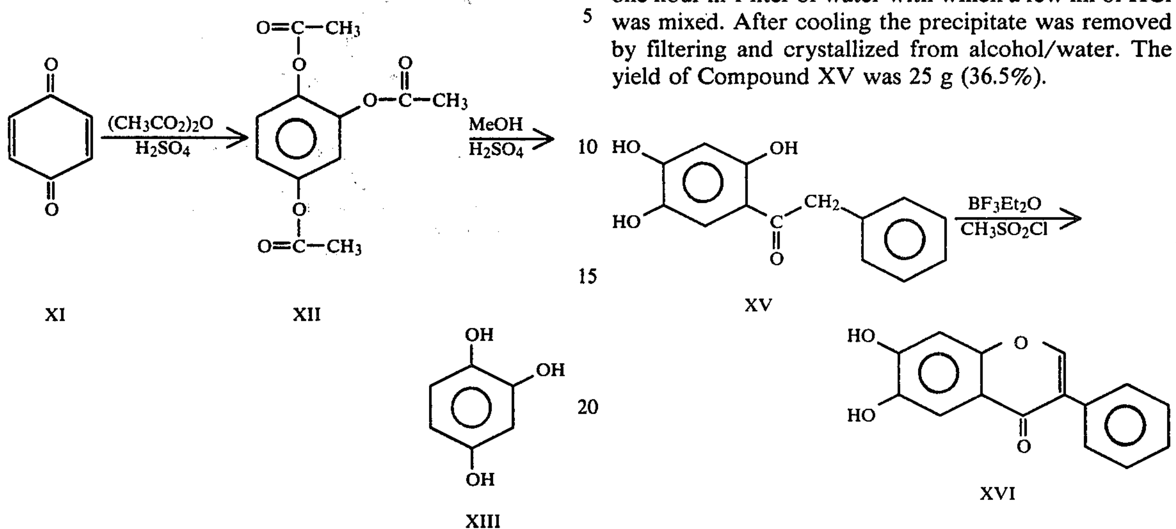

50 g (0.46 mol) 1,4 benzoquinone (XI) was slowly added with stirring to a mixture of 150 g of acetic anhydride and 3 ml of conc. sulfuric acid during which the reaction mixture was cooled so as to keep the temperature between 40° and 50° C. After all of the quinone was dissolved and the heat of formation evolved, the reaction product was washed with an excess of water and the precipitate removed by filtration. Upon drying the precipitate 1,2,4-triacetoxybenzone (XII) was obtained as a light brown powder which can be identified as such after crystallization from methanol. The yield from the reaction was 106 g (91%).

80 g (0.32 mol) of the crude product XII in 200 ml of methanol was heated under reflux for one hour in the presence of 6 g conc. sulfuric acid. The reaction mixture was neutralized with sodium carbonate and then ether added. $Na_2SO_4$ precipitated out and was separated by filtering. Known contaminants were removed by treatment with silica gel resulting in a solution having a dark red color. Upon distillation this solution yielded a dark red oil which rapidly crystallized to a light reddish solid material (XV). The yield of this reaction was 35.4 g (88%).

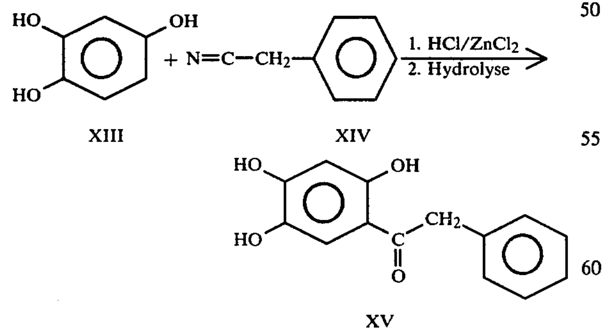

35.4 g (0.28 mol) of Compound XIII was suspended with 30 g water-free $ZnCl_2$ (0.22 mol) in 200 ml dry ether and then mixed with 39.8 g (0.34 mol) benzylcyanide (XIV). Next, dry HCl gas was introduced in the reaction mixture with stirring for four hours at 0° C. After about 70 hours storage in a refrigerator the remaining solution was separated from the oil which had precipitated, washed two times with ether and heated one hour in 1 liter of water with which a few ml of HCl was mixed. After cooling the precipitate was removed by filtering and crystallized from alcohol/water. The yield of Compound XV was 25 g (36.5%).

3.4 g (0.0146 mol) Compound XV was dissolved in 50 ml dry DMF and 7.5 ml borontrifluoride-methyl-etherate added dropwise. Upon heating the solution assumed a yellow-green color. The solution was heated to 50° C. and then 5 g of methanesulfonyl chloride in 25 ml of DMF was added. Heating was continued for 90 minutes at 90°-100° C. and then the reaction mixture was cooled by adding about 0.5 liter water. The resulting yellow precipitate was removed by filtration and after drying yielded 3.1 g of a light brown powder which was purified by crystallization from methanol/water. This provided 3.0 g (81%) of Compound XVI, 6,7-dihydroxy-isoflavone.

EXAMPLE 15

6,7-dihydroxy-isoflavone may be hydrogenated using the methods described in Examples 12 and 13 to prepare the chromanon-4 and chroman respectively. Both of these compounds have been found effective as antioxidants at concentrations as low as 50 parts per million in the standard lard test described in Example 1.

As will be obvious to one skilled in the art, many modifications, variations, substitutions and other alterations can be made in the practices of this invention without departing from the spirit and scope thereof as set forth in the preceding description and examples or in the claims which follow.

What is claimed is:

1. A compound having the structure:

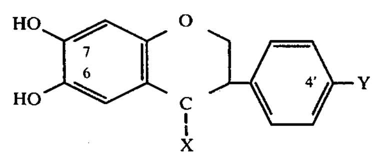

wherein either the dashed line represents two single bonds and X represents two hydrogen atoms or the dashed line represents a double bond and X represents oxygen, and wherein Y may be hydrogen or a hydroxyl, methoxy, or ethoxy group.

2. A compound in accordance with claim 1 having the structure:
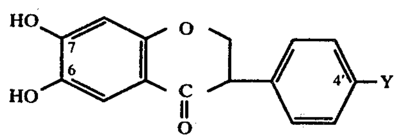
3. A compound in accordance with claim 2 wherein Y is a methoxy group.
4. A compound in accordance with claim 2 wherein Y is hydrogen.
5. A compound in accordance with claim 1 having the structure:
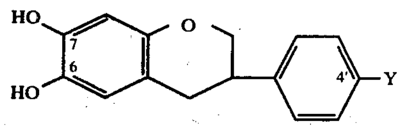
6. A compound in accordance with claim 5 wherein Y is a methoxy group.
7. A compound in accordance with claim 5 wherein Y is hydrogen.
* * * * *